(12) United States Patent
Huggins et al.

(10) Patent No.: US 10,864,384 B2
(45) Date of Patent: Dec. 15, 2020

(54) NON-ACHROMATIC COMPACT GANTRY

(71) Applicant: Varian Medical Systems Particle Therapy GmbH, Troisdorf (DE)

(72) Inventors: Anthony Michael Huggins, Langenfeld (DE); Michael Schillo, Bonn (DE)

(73) Assignee: Varian Medical Systems Particle Therapy GMBH, Troisdorf (DE)

(*) Notice: Subject to any disclaimer, the term of this patent is extended or adjusted under 35 U.S.C. 154(b) by 0 days.

(21) Appl. No.: 16/369,995

(22) Filed: Mar. 29, 2019

(65) Prior Publication Data
US 2020/0306561 A1 Oct. 1, 2020

(51) Int. Cl.
*A61N 5/10* (2006.01)
*H05H 7/00* (2006.01)

(52) U.S. Cl.
CPC .......... *A61N 5/1081* (2013.01); *H05H 7/001* (2013.01); *A61N 2005/1087* (2013.01); *A61N 2005/1095* (2013.01); *H05H 2007/002* (2013.01)

(58) Field of Classification Search
CPC .............. A61N 5/1077; A61N 5/1081; A61N 2005/1085; A61N 2005/1092; A61N 2005/1095; H05H 2007/002
See application file for complete search history.

(56) References Cited

U.S. PATENT DOCUMENTS

| | | | | |
|---|---|---|---|---|
| 8,575,563 | B2* | 11/2013 | Cameron | A61N 5/1077 250/396 ML |
| 9,289,624 | B2* | 3/2016 | Jongen | G21K 5/04 |
| 2009/0296885 | A1* | 12/2009 | Boeh | A61N 5/1042 378/65 |
| 2010/0230620 | A1* | 9/2010 | Tsoupas | A61N 5/1081 250/522.1 |
| 2011/0213239 | A1* | 9/2011 | Amies | A61N 5/1049 600/411 |
| 2013/0289330 | A1* | 10/2013 | Haruna | A61N 5/1081 600/1 |
| 2017/0087390 | A1* | 3/2017 | Johnstone | A61N 5/1081 |
| 2017/0372867 | A1* | 12/2017 | Caspi | H01F 41/048 |
| 2018/0326226 | A1* | 11/2018 | Ebina | H05H 7/001 |
| 2018/0369612 | A1* | 12/2018 | Gerbershagen | A61N 5/1081 |

FOREIGN PATENT DOCUMENTS

EP 3020451 5/2016

* cited by examiner

*Primary Examiner* — David E Smith

(57) ABSTRACT

Embodiments of the present invention provide a compact gantry designed to provide particle therapy using a particle beam. A gantry for providing the particle therapy comprises a first dipole magnet operable to bend a particle beam received from a cyclotron by a first degree amount. The gantry further comprises a plurality of quadrupole magnets configured to condition the beam asymmetrically to produce an asymmetric beam, wherein a configuration of the quadrupole magnets is determined using a dispersion function of a second dipole magnet. Further, the second dipole magnet is operable to receive the asymmetric beam and bend the asymmetric beam by a second degree amount, and wherein the second dipole magnet disperses the asymmetric beam to produce a symmetric beam shape at a treatment iscoenter or at any other reference point.

29 Claims, 6 Drawing Sheets

NON-ACHROMATIC COMPACT GANTRY

FIELD

Embodiments of the present invention generally relate to the field of particle therapy. More specifically, embodiments of the present invention relate to compact gantries used for particle therapy treatment systems.

BACKGROUND

To provide proton or particle therapy treatment to a patient, charged particles are directed to the patient on a treatment table at a chosen angle. A gantry including a beamline and bending magnets are used to bring the charged particle beam to the selected angle relative to the patient table. The charged particles are output from a cyclotron and emitted into the gantry.

A cyclotron is an accelerating device that accelerates protons to high speeds that are approximately two-thirds the speed of light. The cyclotron uses static magnets and radio frequency (RF) to accelerate the protons outwards from the center of the cyclotron in a circular fashion. The protons gain more speed and energy as they move further away from the center. The extraction magnets pull the protons out of the cyclotron and into the beamline. Electromagnets maintain the beam on track and a beam degrader device slows the protons to an optimal energy for treatment. In accordance with physics, the speed at which the proton travels will dictate how far the proton will travel through the patient's body.

A proton beam that is produced by a cyclotron is not purely mono-energetic. This is because some of the protons are accelerated to speeds that are faster than others. Accordingly, the proton beam resembles an energy distribution characterized by an energy spread expressed, typically, as a percentage. The percentage indicates the standard deviation of the energy distribution. In order to compensate for chromatic effects, gantries are typically configured to provide achromatic beam optics.

FIG. 1 illustrates the problem of the dispersion effect in dipole magnets of conventional gantries. As shown in FIG. 1, a higher energy beam 105 traveling through a bending magnet will bend at different angles from a lower energy beam 110. In other words, the bend angle of a proton beam through a bending magnet (e.g., a dipole) is energy dependent and proton beams of varying energies will disperse differently. A bending magnet such as a dipole can, therefore, act as a proton energy filter in this manner.

The dispersion effect can lead to a broadening of the beam in the bending plane. The bending of the beam trajectory in every dipole magnet in a gantry causes the particles with a non-nominal momentum to deviate their trajectory from the nominal axis of the beam. This chromatic phenomenon is called dispersion and is usually described by the so called dispersion function, indicating the deviation from the optical axis of the trajectory of a proton. Dispersion is problematic because in order for the therapy to be delivered effectively to a patient, a proton beam needs to be symmetric at the isocenter. Accordingly, the gantry needs to be designed to have zero or very small dispersion at the treatment isocenter.

To counter for the dispersion effect, conventional gantries are configured with achromatic beam optics. Achromatic beam optics attempt to suppress the dispersion through any bending sections of the gantry at least at the isocenter. Typically, an achromatic system will be configured to suppress the transverse and angular dispersion of the proton beam at the isocenter. However, achromatic beam optics are configured using a combination of magnetic fields that are complicated and typically lead to higher costs and larger systems that are space-prohibitive. In addition, achromatic beam optics require more beamline elements and more drift length in total.

SUMMARY

Embodiments of the present invention provide a compact gantry designed to provide particle therapy using a particle beam. A gantry for providing the particle therapy comprises a first dipole magnet operable to bend a particle beam received from a cyclotron by a first degree amount. The gantry further comprises a plurality of quadrupole magnets configured to condition the beam asymmetrically to produce an asymmetric beam, wherein a configuration of the quadrupole magnets is determined using a dispersion function of a second dipole magnet. Further, the second dipole magnet is operable to receive the asymmetric beam and bend the asymmetric beam by a second degree amount, and wherein the second dipole magnet disperses the asymmetric beam to produce a symmetric beam shape at a treatment iscoenter or at any other reference point.

In one embodiment, a gantry for a proton radiation therapy system is presented. The gantry comprises at least one first dipole magnet operable to bend a proton beam received from a cyclotron by a first degree amount. The gantry further comprises a plurality of quadrupole magnets configured to condition the proton beam asymmetrically to produce an asymmetric proton beam, wherein a configuration of the quadrupole magnets is determined using a dispersion function of a second dipole magnet, and wherein the plurality of quadrupole magnets are positioned in-line between the first and second dipole magnets. Further, the gantry comprises the second dipole magnet operable to receive the asymmetric proton beam and bend the asymmetric proton beam by a second degree amount, and wherein the second dipole magnet disperses the asymmetric proton beam to produce a symmetric beam shape at a treatment iscoenter.

In another embodiment, a method for performing proton radiation therapy is disclosed. The method comprises receiving a proton beam emitted from a cyclotron and bending the proton beam by a first degree amount using a first dipole magnet. In one embodiment, the first dipole magnet may comprise multiple dipole magnets. The method further comprises conditioning the proton beam asymmetrically to produce an asymmetric proton beam, wherein the conditioning comprises a calculation accounting for a dispersion function of a second dipole magnet. Finally, the method comprises bending the asymmetric proton beam by a second degree amount using the second dipole magnet, wherein the second dipole magnet disperses the asymmetric proton beam to produce a symmetric bean shape at a treatment iscoenter.

In one embodiment, a compact radiation therapy system is presented. The system comprises a cyclotron operable to emit a beam that is compact. In one embodiment, the beam may comprise a proton beam. The system further comprises a gantry coupled to the cyclotron and comprising: a) a first dipole magnet operable to bend a proton beam received from a cyclotron by a first degree amount; b) a second dipole magnet; c) a degrader configured to reduce an energy of the proton beam; d) one or more quadrupole magnets configured to condition the proton beam asymmetrically to produce an asymmetric proton beam, wherein a configuration of the one or more quadrupole magnets is determined using a dispersion function of a second dipole magnet, and wherein the one or more quadrupole magnets are positioned in-line between the first and second dipole magnets; and e) wherein the second dipole magnet is operable to receive the asymmetric proton beam and bend the asymmetric proton beam by a second degree amount, and wherein the second dipole magnet disperses the asymmetric proton beam to produce a symmetric bean shape at a treatment iscoenter.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Non-Achromatic Compact Gantry

Embodiments of the present invention provide a non-achromatic compact gantry designed to provide particle therapy using a compact beam with acceptable beam properties at the isocenter. The particles may be protons or other charged particles. The non-achromatic compact gantry of the present invention would not require the complex hardware that is required to suppress the dispersion function of the bending dipole in achromatic systems. In other words, embodiments of the present invention produce acceptable symmetric beam properties at the isocenter without suppressing the dispersion functions (e.g., of the bending dipole). Embodiments of the present invention, therefore, reduce the number of beamline elements in the gantry, thereby, resulting in a gantry design that is advantageously more compact and cost-effective.

According to one embodiment, a round beam cross-section is produced at the isocenter by taking the dispersion effect of the last dipole in the beamline into account and using it to produce a round beam cross-section at the isocenter rather than correcting for the dispersion effect of the last dipole. In order to use the dispersion effect of the last dipole in the beamline advantageously, embodiments of the present invention transmit an expected asymmetric beam profile to the last dipole. The chromatic effects of the last dipole cause the beam to disperse and become symmetric and round at the isocenter (or any other point of interest).

Figure 1:
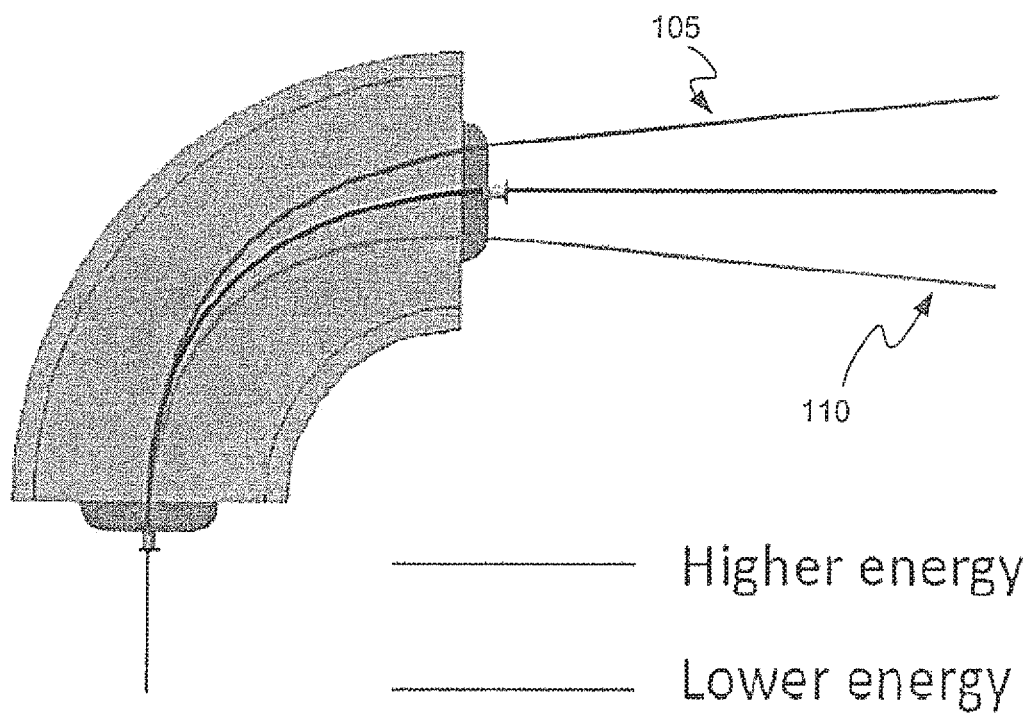
FIG. 1 illustrates the problem of the dispersion effect in conventional gantries.
Figure 2:
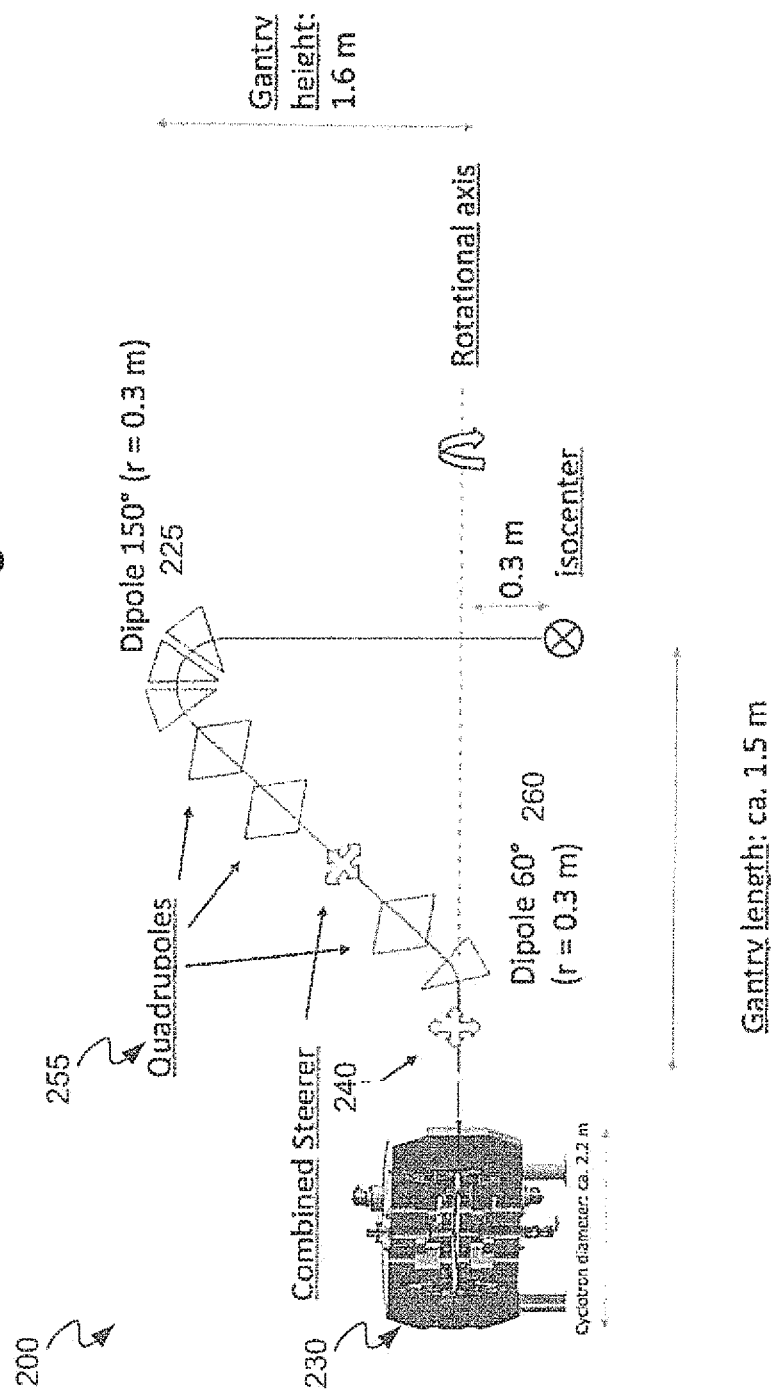
FIG. 2 depicts an exemplary conventional cyclotron and compact gantry including a bending magnet according to embodiments of the present invention.

FIG. 2 depicts an exemplary compact gantry 200 in accordance with embodiments of the present invention. In one embodiment, gantry 200 comprises a superconducting bending magnet 225 with a bending angle of approximately 150 degrees. Superconducting magnets are generally far lighter than comparable conventional magnets and avoid large beam losses in the degrader section which eliminates beam loss to the patient. The inclusion of a superconducting bending magnet also enables less radiation shielding to be used and less physical space is required to accommodate the beam therapy system. It should be noted, however, that in other embodiments of the invention, other types of magnets may be used for the bending dipole 225 as long as the dispersion function of the bending dipole 225 can be determined accurately in order to achieve a round beam cross-section at the isocenter. In one embodiment, the gantry 200 can be a monoenergetic gantry.

In the example of FIG. 2, gantry 200 includes a first bending dipole 260 having an angle of approximately 60 degrees for bending the beam produced by cyclotron 230. It should be noted that the first bending dipole 260 may also comprise multiple dipoles instead of only a single dipole. The gantry is supported by a physical containment and supporting structure (not pictured) having an emitter side that emits a charged particle beam for treatment and a receiver side operable to receive the charged particle beam produced by the cyclotron. In one embodiment, a set of combined steerers 240 may be used to shift the beam in a direction without focusing the beam. It should be noted, however, that the use of steerers is not critical to embodiments of the present invention.

In one embodiment, the upward portion of the beamline can include one or more (e.g., three) small quadrupole magnets 255 to focus the beam in an asymmetric fashion to compensate for the dispersion of the last bend caused by bending magnet 225. In one embodiment, e.g., if the beam produced has a fixed output energy, the beamline components used to implement gantry 200 can be relatively small in size due to the small size of the beam generated by the cyclotron. The magnetic field used to generate the beam can remain unchanged during treatment and does not require multiple ramping stages. However, a specific ramping speed may be required for maintenance and recovery, for example. The protons exiting the cyclotron may be, for example, at an energy of 230 MeV.

Figure 3:
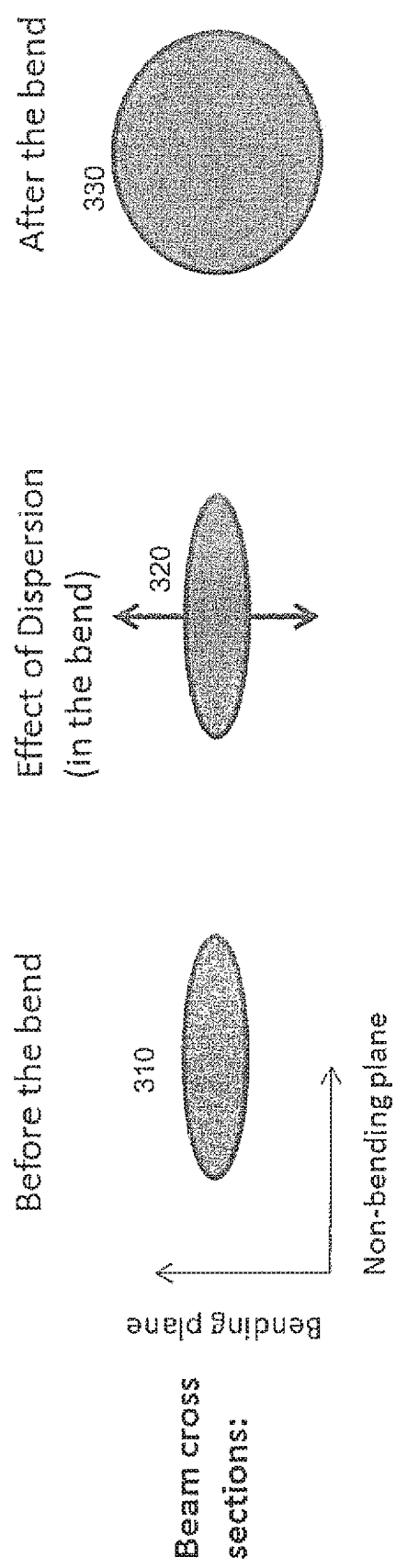
FIG. 3 illustrates the manner in which taking into account the dispersion effect of the last bending dipole results in achieving a symmetric beam shape (cross section) in accordance with embodiments of the present invention.

In one embodiment of the present invention, instead of correcting for the dispersion effect of dipole 225 (as is the case with conventional achromatic systems), the dispersion effect of the bending magnet is taken into account in order to achieve a round spot shape at the isocenter. FIG. 3 illustrates the manner in which taking into account the dispersion effect of the last bending dipole advantageously results in achieving a round beam cross-section in accordance with embodiments of the present invention.

In one embodiment of the present invention, a beam is prepared asymmetrically (e.g., by using beamline elements such as quadrupoles) before the final bend in the beamline. In other words, the beam is conditioned to be asymmetric prior to the last bend by taking into account the dispersion effect of the bending dipole 225. Accordingly, prior to the last bend, the beam has an asymmetric shape as shown by beam cross-section 310. It should be noted that it is important to calculate the dispersion effect of the last bending dipole in the beamline accurately in order to prepare the beam prior to the bend. Determining the dispersion effect of the dipole 225 accurately ensures that a round shape is achieved at the isocenter (or any other desired point of interest).

The last bending dipole, as a result of its chromatic effects, stretches the beam in the bending plane as illustrated by beam cross-section 320. If the beam is prepared asymmetrically by accurately accounting for the dispersion effect of the bending dipole 225, the resulting shape at the isocenter is symmetric and round as illustrated by beam cross-section 330.

Figure 4:
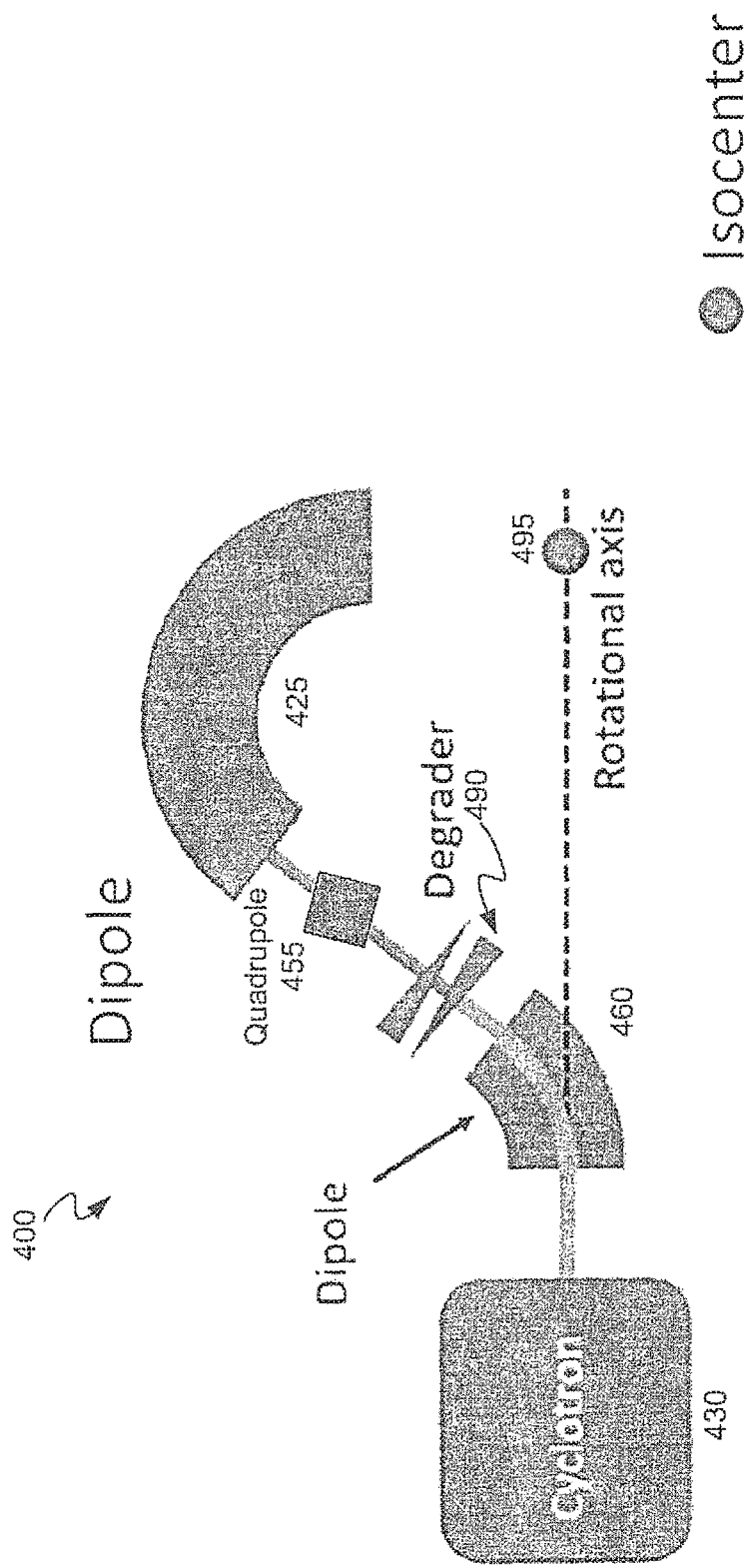
FIG. 4 depicts an exemplary compact gantry in accordance with embodiments of the present invention.

FIG. 4 depicts an exemplary compact gantry 400 in accordance with embodiments of the present invention. The gantry comprises a first bending dipole 460 for bending the beam produced by cyclotron 430. As noted above, instead of a single dipole, the first bending dipole may comprise more than one dipole positioned before the degrader 490. The gantry may also comprise a degrader 490 that adjusts the energy produced by the cyclotron 430, e.g., a degrader may reduce the energy to a required value. In one embodiment, gantry 400 comprises a bending dipole 425.

In one embodiment, the upward portion of the beamline can include one or more quadrupole magnets 455 to focus the beam. For example, in one embodiment, quadrupole magnet(s) 455 can be used to prepare the beam asymmetrically prior to the final bend, where the asymmetric shape of the beam prepared by the quadrupole magnet(s) takes into account the dispersion function of the bending dipole 425.

In gantries where the energy of the proton beam is adjusted or reduced by means of a degrader, the energy spread within the beam is dependent on the energy of the beam. For example, the lower the beam energy, the larger the energy spread. This is an artifact produced by the degrader. The dispersion effect of the bending dipole 455 will be different for an energy spread as well as different beam energies. In one embodiment, where gantry 400 produces a single maximum energy beam, the calculation required to account for the dispersion function of the bending dipole 425 is relatively simple. In other words, if the proton beam comprises a fixed output energy, e.g., 220 MeV, only a single calculation may be required to determine the manner in which to condition the beam asymmetrically prior to the last bend and this may be a relatively straightforward calculation. The gantry, for example, may produce a single fixed output energy where no energy modulation takes place prior to any bend of the beamline. Hence, the bend, e.g., the final dipole 425 only needs to deal with the beam (and corresponding proton energies) as produced by the cyclotron (and other minimal effects from scattering in the vacuum window foils are neglected).

On the other hand, in a different embodiment, where the proton beam comprises an energy spread, further calculations and parameterizations may be required to condition the beam appropriately before the final bend in order to attain a sufficiently round spot shape at the isocenter.

In one embodiment, the one or more dipoles in the gantry may be high-field dipoles. For example, dipole 425 may be a high-field dipole comprising an iron-based electromagnet or a superconducting magnet. High-field dipoles have stronger magnetic fields. One of the advantages of a high-field dipole magnet is that it reduces the dispersion effect of the dipole as a result of shorter proton travel length through the bend. This allows the dispersion effect of the dipole to be calculated easily, which in turn means that the beam can be conditioned asymmetrically to account for the dispersion effect with relatively less complex calculations. Accordingly, embodiments of the present invention preferably employ a high-field dipole magnet for at least the final bend.

In one embodiment of the present invention, one or more quadrupoles (e.g., quadrupole 455) may be used to shape and condition the beam asymmetrically upstream from the bending dipole 425. Conditioning the beam is important because a degrader, e.g., degrader 490, while adjusting or reducing the energy of the beam will often distort the shape of the beam as a result of scattering effects. Quadrupoles are typically used to constrain, confine and shape the proton beam in a desired way. The placement and number of quadrupoles may vary. It should be noted that in this embodiment, the quadrupoles not only constrain and shape the beam to maintain the beam confined along the beamline, but the quadrupoles also prepare the beam asymmetrically (using calculations involving the dispersion effect of the last dipole) in a way such that the dispersion of the last dipole 225 produces a symmetric beam at the isocenter.

In different embodiments, other types of magnets besides quadrupoles may be used to condition the beam effectively. For example, different types of multipole magnets may be used. By way of example, octopoles may be used. In other embodiments, instead of magnets, collimators may also be used to prepare the beam following the degrader. In other words, a collimator may be used to define a new beam size and shape following the degrader. An advantage of using collimators is that they are typically more cost-effective as compared to quadrupoles.

As noted above, embodiments of the present invention are advantageous as compared to conventional systems using achromatic beam optics that require more beamline elements with longer corresponding drift lengths. By not suppressing the dispersion effect of the last dipole, embodiments of the present invention allow the beamline to be simplified leading to a more compact gantry. For example, as shown in FIG. 2, embodiments of the present invention result in advantageous gantry sizes of 1.6 m or less.

Instead of introducing beamline elements to suppress the dispersion effect of the last dipole, embodiments of the present invention use the dispersion effect of the last dipole advantageously in such a way to produce a symmetric beam at the isocenter. Embodiments of the present invention condition the beam asymmetrically prior to the last bend in the beamline (using the calculated dispersion effect of the last dipole) such that a round spot shape is produced at the isocenter after the beam has passed through the last dipole 425.

In conventional achromatic systems, the dispersion effect is suppressed by combining the effects of the two bending dipoles in the gantry in addition to using several quadrupoles within the beamline. Alternatively, a special type of bending dipole (for suppressing the dispersion effect) was needed to be designed with several magnetic elements besides just a dipole field, e.g., several quadrupoles and sextupoles, etc.

By not suppressing the dispersion function, embodiments of the present invention obviate the need for combining the effects of the two dipoles. In other words, dipole 425 is decoupled from and operates independently of dipole 460. Further, dipole 425 can simply comprise a dipole field without needing several other elements that were used in achromatic systems to suppress the dispersion function.

In one embodiment of the present invention, a symmetric round beam can be presented to degrader 490 by accounting for the dispersion effect created by the first bending dipole 460. In other words, the same concept that is used to produce a round spot shape at the isocenter 495 can also be used for the optics from the cyclotron 430 to the degrader 490.

Typically, a beam provided by the cyclotron 430 will not be shaped in a way that is suitable for treatment. One or more optional quadrupoles (not shown in FIG. 4) placed in the beamline prior to the first bending dipole 460 can condition and shape the beam to produce an asymmetric beam at dipole 460 that appropriately takes into consideration the dispersion effect of dipole 460. If the dispersion effect of dipole 460 is properly accounted for and calculated, the dipole 460 would broaden the asymmetric beam (in the bending plane) to produce a symmetric round beam at the degrader 490. Embodiments of the present invention are able to, therefore, advantageously incorporate the degrader 490 within the beamline between the first bending dipole 460 and the last bending dipole 425. In conventional gantries, by comparison, the degrader needs to be placed right after the cyclotron 430, where two or more dipoles are needed following the degrader to address dispersion effects from the degrader. By allowing the degrader to be mounted between the two final dipoles (e.g., dipoles 460 and 425) in the beamline, the size and the cost of the gantry are significantly reduced.

In one embodiment of the present invention the degrader may be mounted after the last dipole 425 before the beam reaches the patient.

Figure 5:
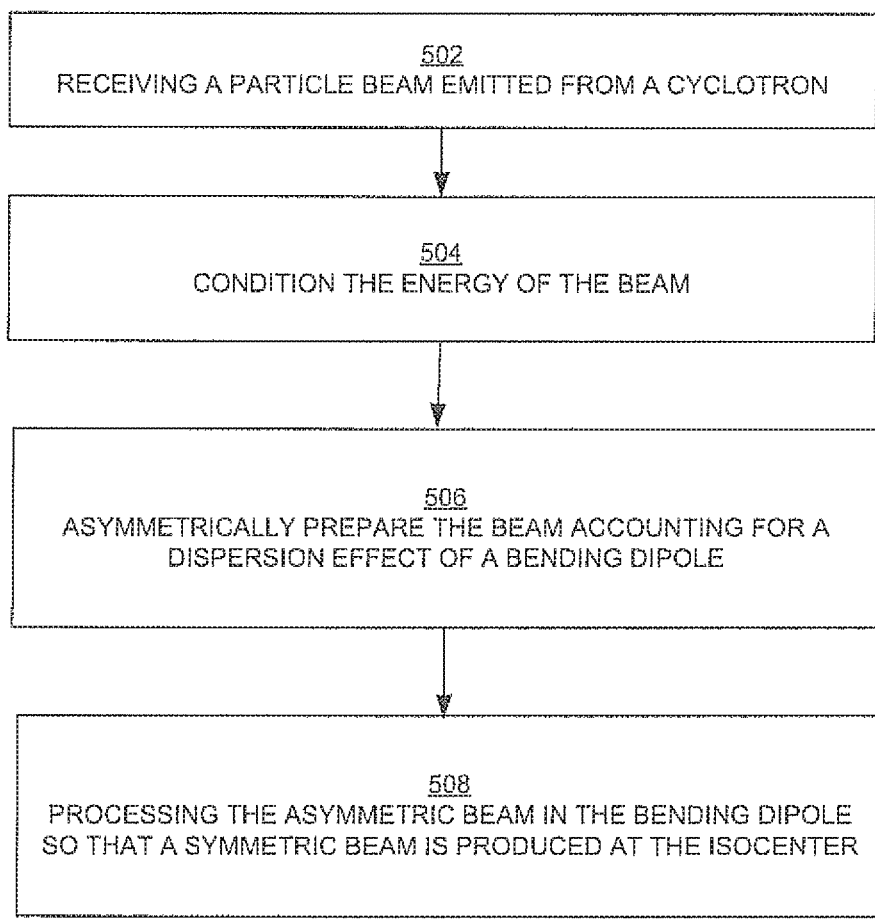
FIG. 5 illustrates a flowchart of an exemplary computer controlled process for performing radiation therapy in accordance with one embodiment of the present invention.

FIG. 5 illustrates a flowchart 500 of an exemplary process for performing radiation therapy in accordance with one embodiment of the present invention.

At step 502, a particle beam is emitted from a cyclotron and received into the beamline of the gantry.

At step 504, the energy of the beam is conditioned.

At step 506, the beam is asymmetrically prepared to account for a dispersion effect of the last bending dipole in the beamline. As mentioned above, quadrupoles or other elements, e.g., a collimator may be used to condition the beam asymmetrically.

At step 508, the asymmetric beam passes through the last bending dipole in the beamline such that it is dispersed in the bend to produce a symmetric round shape at the isocenter.

Figure 6:
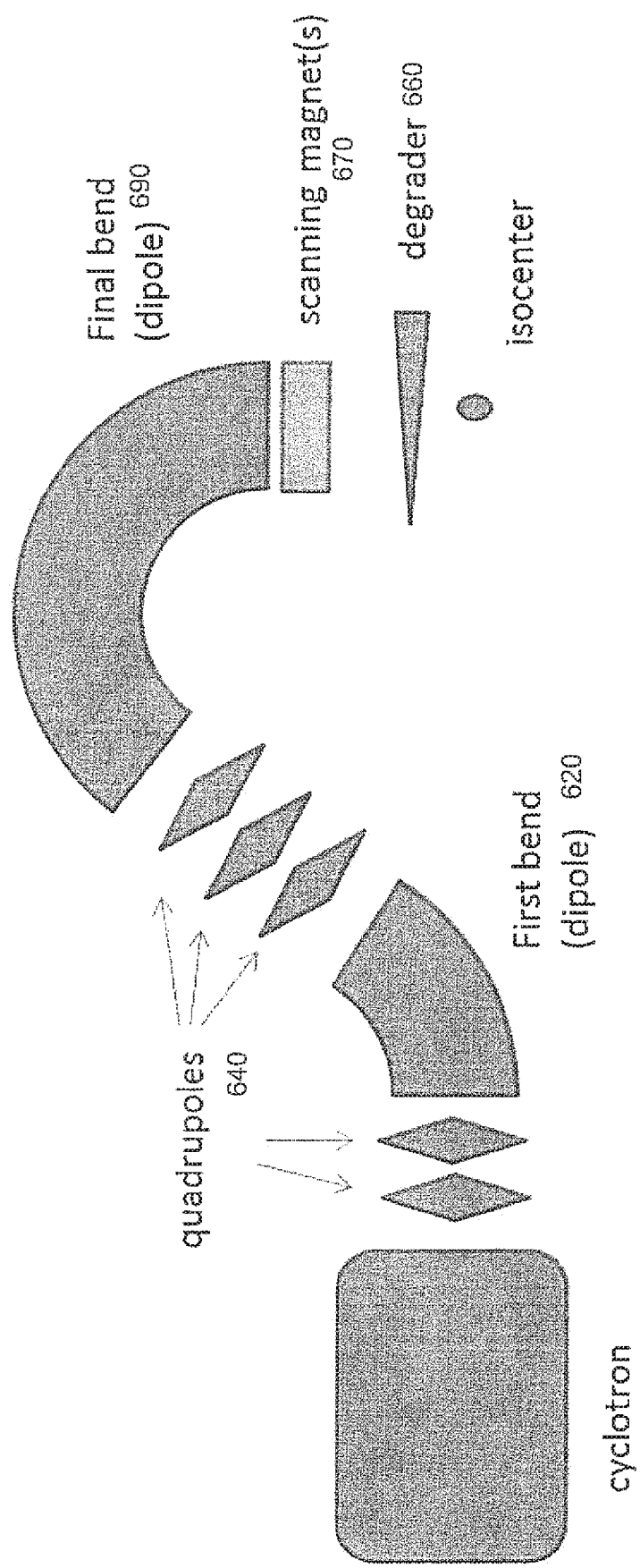
FIG. 6 illustrates an exemplary compact gantry in which the degrader is positioned downstream from the final bend in accordance with embodiments of the present invention.

FIG. 6 illustrates an exemplary compact gantry in which the degrader is positioned downstream from the final bend in accordance with embodiments of the present invention.

As noted above, in one embodiment of the present invention the degrader may be mounted after the last dipole 690 before the beam reaches the patient. FIG. 6 illustrates an embodiment where the degrader is placed between the final bend and the patient. The degrader, in one embodiment, may include a collimation system. Any of a number of well known collimation systems can be used. As noted above, collimators may be used to prepare the beam following the degrader. In other words, a collimator may be used to define a new beam size and shape following the degrader.

In one embodiment, the collimation system may be static, while in another system the collimation system may be dynamic. The collimation system may comprise any type of material (e.g. metal) to cut out parts of the beam. In a dynamic version of the collimation system, the position of the collimating material is adaptable during the treatment, e.g. to follow the deflected beam position or to be in sync with the beam range, e.g., the degrader settings. The adjustable collimation system ensures sharp edges to the scanning field.

In the embodiment shown in FIG. 6, scanning magnet or magnets 670 are positioned downstream of the final bend as well but before the degrader 660. In different embodiments, the scanning magnets 670 may be located upstream of the final bend. The scanning magnets can comprise one or two deflection magnets that change the angle of the beam. This way the typically narrow beam (approximately 1 cm in diameter) can be directed to the desired location in a two-dimensional treatment field. The beam will be scanned across the target area and the depth will be varied with the degrader.

In the embodiment illustrated in FIG. 6, the degrader is positioned as close to the patient as possible. This prevents the degrader from scattering the beam too significantly before the beam reaches the patient. Further, the collimation system included with the degrader 660 (not shown in FIG. 6) will also help ensure a symmetric beam shape at the isocenter. Accordingly, the embodiment in FIG. 6 achieves a symmetric beam at the degrader position. Consequently, the beam will then also be symmetric at the isocenter (patient). In other words, in the embodiment of FIG. 6, a symmetric beam profile can be achieved at a desired point of interest, e.g., at the degrader position, and not necessarily at the isocenter.

It should be noted that the number of quadrupoles 640, the location of the scanning magnet(s) 670 and the assembly of the degrader 660 illustrated in FIG. 6 are purely exemplary. Different systems may be designed with a different number of quadrupoles, for example, or the degrader may have an assembly that comprises several thin sheets.

Embodiments of the present invention are thus described. While the present invention has been described in particular embodiments, it should be appreciated that the present invention should not be construed as limited by such embodiments, but rather construed according to the following claims.

What is claimed is:

1. A gantry for a radiation therapy system, the gantry comprising:
   at least one first dipole magnet operable to bend a beam received from a cyclotron by a first degree amount;
   a second dipole magnet disposed at the last bend of a beamline; and
   a plurality of quadrupole magnets disposed in-line between the at least one first dipole magnet and the second dipole magnet, and configured to condition the beam to produce an asymmetric beam having an amount of asymmetry based on a dispersion function of the second dipole magnet;
   wherein the second dipole magnet is operable to receive the asymmetric beam and bend the asymmetric beam by a second degree amount, and wherein the second dipole magnet disperses the asymmetric beam according to the dispersion function to account for the amount of asymmetry and produce a round beam cross-section at a treatment isocenter.

2. The gantry of claim 1, wherein the beam is a proton beam.

3. The gantry of claim 2, wherein the proton beam comprises an energy spread.

4. The gantry of claim 1 wherein the first degree amount is approximately 60 degrees and wherein the second degree amount is approximately 150 degrees.

5. The gantry of claim 1, wherein the gantry has a height of approximately 1.6 m.

6. The gantry of claim 1, wherein the second dipole magnet is a superconducting bending magnet.

7. The gantry of claim 1, further comprising:
a degrader operable to reduce an energy of the proton beam received from the cyclotron.

8. The gantry of claim 7, wherein the degrader is positioned in-line between the at least one first dipole magnet and the plurality of quadrupole magnets.

9. The gantry of claim 7, wherein the degrader is disposed subsequent to the second dipole magnet and prior to the treatment isocenter.

10. The gantry of claim 1, wherein the at least one first dipole magnet and the second dipole magnet comprise high-field dipole magnets.

11. A method for performing radiation therapy, the method comprising:
receiving a particle beam emitted from a cyclotron;
bending the beam by a first degree amount using a first dipole magnet;
conditioning the beam asymmetrically to produce an asymmetric beam, wherein the conditioning comprises introducing an amount of asymmetry into the particle beam that based on a dispersion function of a second dipole magnet disposed at the last bend of a beamline; and
bending the asymmetric beam by a second degree amount using the second dipole magnet, wherein the second dipole magnet disperses the asymmetric beam according to the dispersion function to account for the amount of asymmetry and produce a round beam cross-section at a treatment iscoenter.

12. The method of claim 11, wherein the conditioning is performed using one or more quadrupole magnets disposed in-line between the first dipole magnet and the second dipole magnet.

13. The method of claim 11, wherein the conditioning is performed using a plurality of multipole magnets disposed in-line between the first dipole magnet and the second dipole magnet.

14. The method of claim 11, wherein the conditioning is performed using one or more octopole magnets disposed in-line between the first dipole magnet and the second dipole magnet.

15. The method of claim 11, wherein the conditioning is performed using one or more collimators disposed in-line between the first dipole magnet and the second dipole magnet.

16. The method of claim 11, further comprising:
prior to the conditioning, reducing an energy of the particle beam using a degrader, wherein the degrader is positioned in-line between the first dipole magnet and the second dipole magnet.

17. A compact radiation therapy system, comprising:
a cyclotron operable to emit a beam that is compact;
a gantry coupled to the cyclotron and comprising:
a first dipole magnet operable to bend the beam received from the cyclotron by a first degree amount;
a second dipole magnet disposed at the last bend of a beamline;
a degrader configured to reduce an energy of the beam; and
one or more quadrupole magnets disposed in the beamline between the at least one first dipole magnet and the second dipole magnet, and configured to condition the beam to produce an asymmetric beam having an amount of asymmetry based on a dispersion function of the second dipole magnet;
wherein the second dipole magnet is operable to receive the asymmetric beam and bend the asymmetric beam by a second degree amount, and wherein the second dipole magnet disperses the asymmetric beam according to the dispersion function to account for the amount of asymmetry and produce a round beam cross-section at a point of interest.

18. The compact radiation therapy system of claim 17, wherein the second dipole magnet is a superconducting bending magnet and wherein further the beam comprises a proton beam.

19. The compact radiation therapy system of claim 17, wherein the degrader is positioned in-line between the first dipole magnet and the one or more quadrupole magnets.

20. The compact radiation therapy system of claim 17, wherein the first dipole magnet and the second dipole magnet comprise high-field dipole magnets.

21. The compact radiation therapy system of claim 17, wherein the beam is a proton beam of a fixed output energy.

22. The compact radiation therapy system of claim 17, wherein the one or more quadrupole magnets are positioned in-line between the degrader and the second dipole magnet.

23. The compact radiation therapy system of claim 17, wherein the degrader is disposed between the second dipole magnet and the point of interest.

24. The compact radiation therapy system of claim 23, wherein the degrader comprises a collimation system.

25. The compact radiation therapy system of claim 24, wherein the collimation system is dynamic, and wherein a position of the collimation system is adjustable during treatment.

26. The compact radiation therapy system of claim 23, wherein the point of interest is at a location of the degrader.

27. The compact radiation therapy system of claim 23, wherein the point of interest is located at a treatment isocenter.

28. The compact radiation therapy system of claim 17, further comprising a quadrupole magnet positioned before the first dipole magnet.

29. The compact radiation therapy system of claim 17, further comprising a scanning magnet and wherein the scanning magnet is positioned between the second dipole magnet and the degrader.

* * * * *